(12) United States Patent
Williams et al.

(10) Patent No.: US 9,844,514 B2
(45) Date of Patent: Dec. 19, 2017

(54) METHODS FOR TREATING AN ESTABLISHED MYOCARDIAL INFARCTION

(71) Applicant: UNIVERSITY OF LOUISVILLE RESEARCH FOUNDATION, INC., Louisville, KY (US)

(72) Inventors: Stuart K. Williams, Harrods Creek, KY (US); James B. Hoying, Louisville, KY (US); Amanda J. LeBlanc, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 14/327,497

(22) Filed: Jul. 9, 2014

(65) Prior Publication Data

US 2014/0370069 A1    Dec. 18, 2014

Related U.S. Application Data

(63) Continuation-in-part of application No. 14/348,584, filed as application No. PCT/US2012/058378 on Oct. 1, 2012.

(60) Provisional application No. 61/844,267, filed on Jul. 9, 2013, provisional application No. 61/542,105, filed on Sep. 30, 2011.

(51) Int. Cl.
*A61K 9/70* (2006.01)
*A61K 35/35* (2015.01)

(52) U.S. Cl.
CPC ............... *A61K 9/70* (2013.01); *A61K 35/35* (2013.01)

(58) Field of Classification Search
CPC .................................. A61K 9/70; A61K 35/35
See application file for complete search history.

(56) References Cited

U.S. PATENT DOCUMENTS

| | | | |
|---|---|---|---|
| 2002/0142458 A1* | 10/2002 | Williams et al. | 435/366 |
| 2003/0007954 A1* | 1/2003 | Naughton et al. | 424/93.7 |
| 2008/0226726 A1 | 9/2008 | Jaconi et al. | |
| 2011/0218396 A1 | 9/2011 | Williams et al. | |
| 2012/0201890 A1 | 8/2012 | Williams et al. | |

FOREIGN PATENT DOCUMENTS

WO    2013049862    4/2013

OTHER PUBLICATIONS

Raghavan et al. "Timing of bypass surgery in stable patients after acute myocardial infarction" (2007), Canadian Journal of Cardiology, vol. 23, No. 12: 976-982.*
PCT Search Report Application No. PCT/US14/46052, dated Oct. 16, 2014.

* cited by examiner

*Primary Examiner* — Robert Yamasaki
*Assistant Examiner* — Teresa E Knight
(74) *Attorney, Agent, or Firm* — Conley Rose PC

(57) ABSTRACT

This application discloses methods for treating an established myocardial infarction, including treatment with an epicardial construct containing stromal vascular fraction (SVF) from adipose tissue which may be seeded onto a biocompatible substrate, which preserves microvascular function and LV contractile mechanisms.

9 Claims, 19 Drawing Sheets

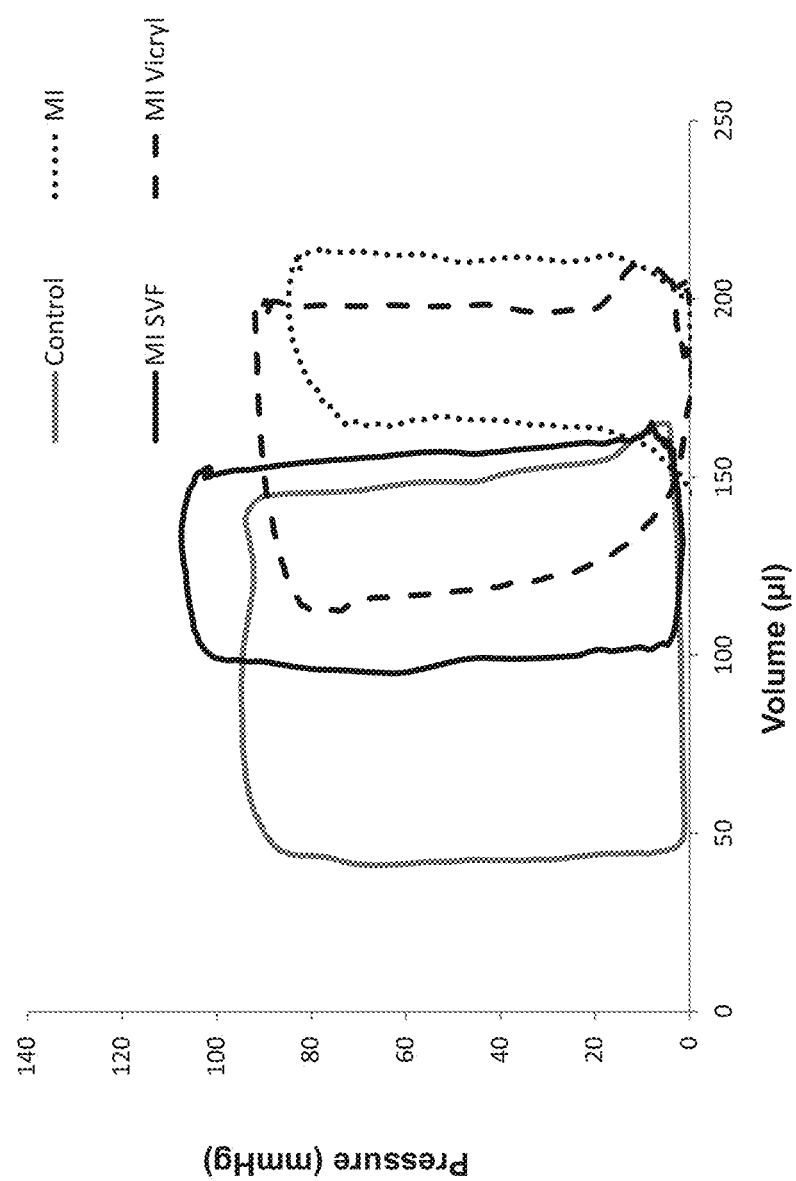

Fig. 1B

| Hemodynamic Parameter | MI<br>n = 8 | MI SVF<br>n = 8 | MI Vicryl<br>n = 7 | ANOVA p-value |
|---|---|---|---|---|
| HR (min-1) | 268.6 ± 8.6 | 267.5 ± 11.6 | 270.6 ± 8.0 | 0.878 |
| CO (mL/min) | 20.9 ± 1.4 | 20.5 ± 2.6 | 26.5 ± 1.5 | 0.077 |
| ESP (mmHg) | 93.3 ± 7.8 | 94.9 ± 5.8 | 88.9 ± 3.3 | 0.247 |
| EDP (mmHg) | 5.4 ± 0.6 | 6.7 ± 1.0 | 6.0 ± 0.6 | 0.512 |
| ESV (µL) | 148.4 ± 25.7 | 90.3 ± 16.3 | 94.5 ± 15.0 | 0.092 |
| EDV (µL) | 211.8 ± 23.4 | 159.1 ± 14.0 | 185.3 ± 15.8 | 0.144 |
| SV (µL) | 78.8 ± 7.0 | 76.5 ± 8.4 | 97.8 ± 4.3 | 0.094 |
| EF (%) | 39.9 ± 5.5 | 48.6 ± 6.5 | 53.2 ± 4.0 | 0.256 |
| +dP/dt (mmHg/s) | 7601 ± 419 | 7372 ± 289 | 8281 ± 252 | 0.174 |
| -dP/dt (mmHg/s) | -5341 ± 486 | -6342 ± 467 | -5982 ± 380 | 0.293 |
| Emax (mmHg/µl) | 0.55 ± 0.07 * | 1.4 ± 0.2 | 0.5 ± 0.06 * | <0.001 |
| EDPVR slope (mmHg/µl) | 0.07 ± 0.01 | 0.1 ± 0.03 | 0.08 ± 0.02 | 0.590 |

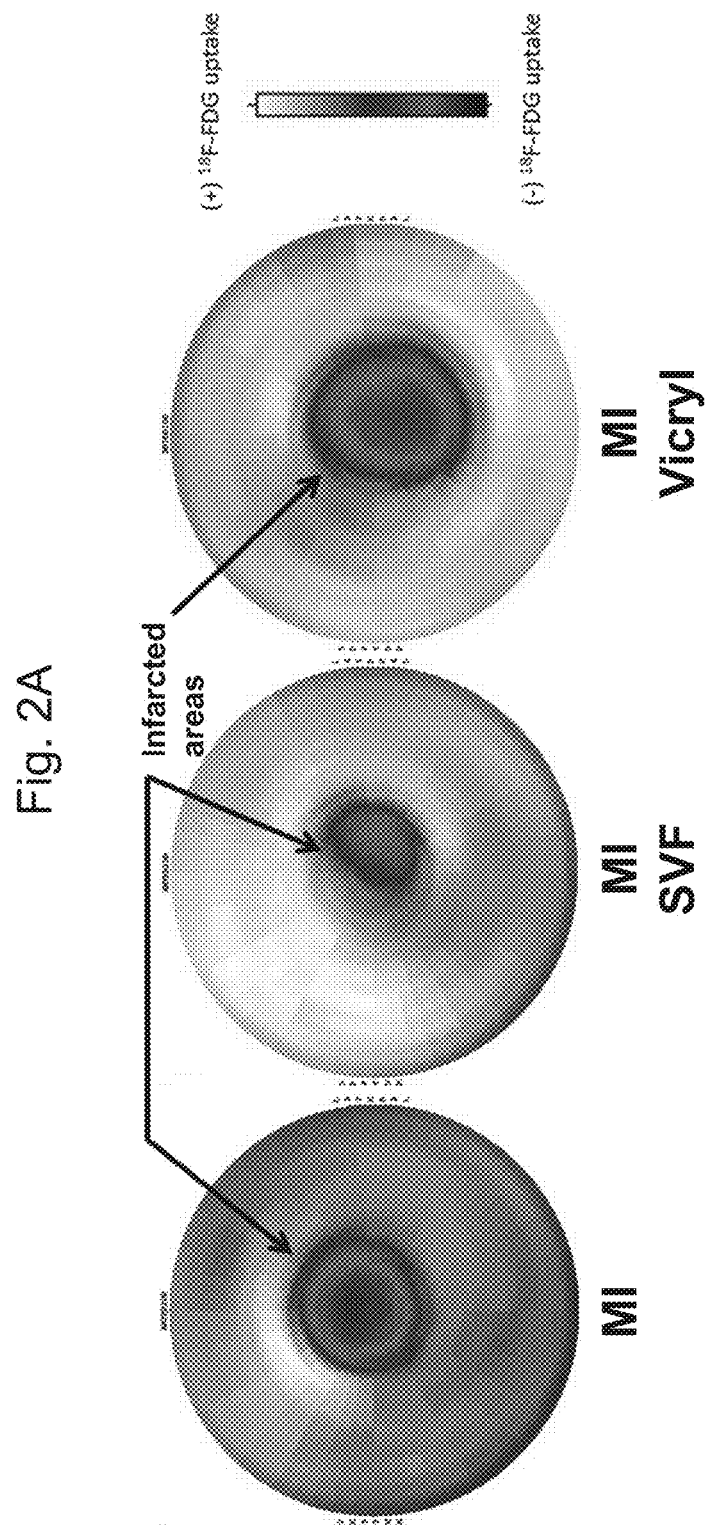

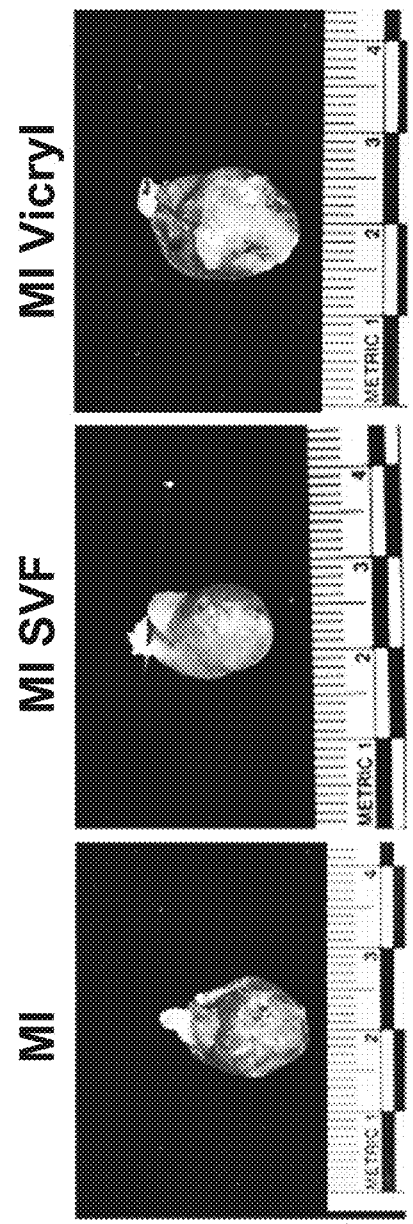

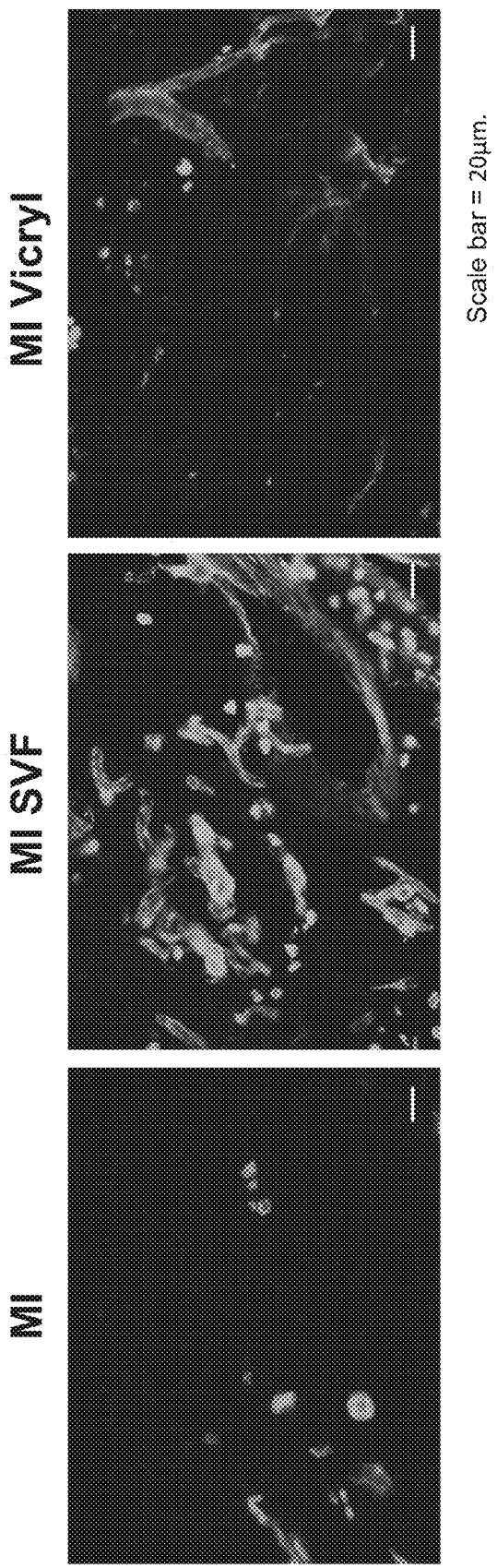

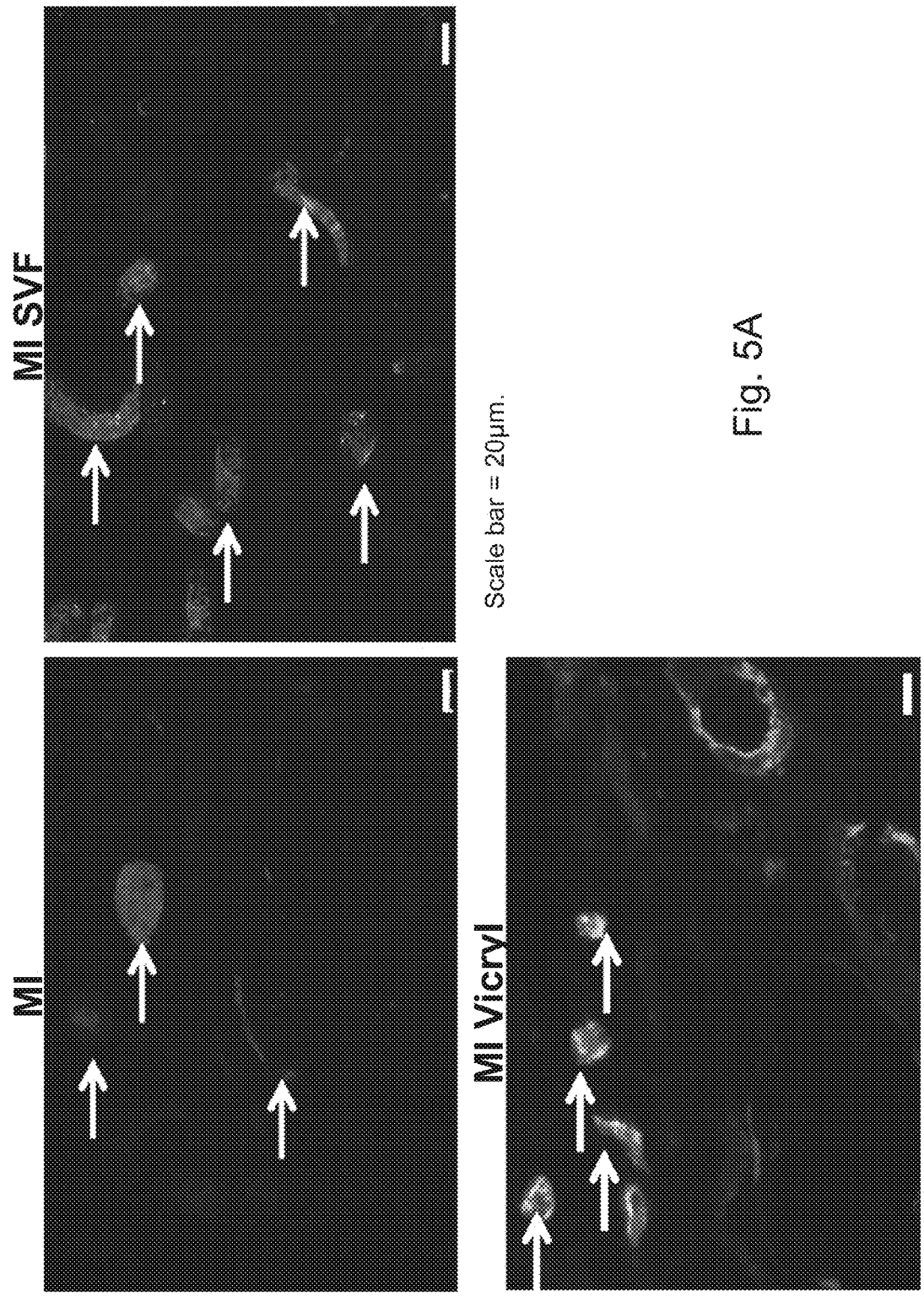

Fig. 6B

| Hemodynamic Parameter | MI 2wk (n = 7) | MI SVF (n = 8) | T-test p-value |
|---|---|---|---|
| HR (min-1) | 286.9 ± 8.7 | 267.5 ± 11.6 | 0.215 |
| CO (mL/min) | 22.0 ± 2.1 | 20.5 ± 2.6 | 0.665 |
| ESP (mmHg) | 81.6 ± 1.5 | 94.9 ± 5.8 | 0.060 |
| EDP (mmHg) | 6.7 ± 1.0 | 6.7 ± 1.0 | 0.970 |
| ESV (μL) | 88.9 ± 19.6 | 90.3 ± 16.3 | 0.956 |
| EDV (μL) | 155.0 ± 20.1 | 159.1 ± 14.0 | 0.867 |
| SV(μL) | 76.9 ± 7.8 | 76.5 ± 8.4 | 0.971 |
| EF (%) | 51.1 ± 5.5 | 48.6 ± 6.5 | 0.774 |
| +dP/dt (mmHg/s) | 7332 ± 311 | 7372 ± 289 | 0.928 |
| -dP/dt (mmHg/s) | -5205 ± 266 | -6342 ± 467 | 0.0629 |
| Emax (mmHg/μl) | 1.0 ± 0.1 | 1.4 ± 0.2 | 0.152 |
| EDPVR slope (mmHg/μl) | 0.06 ± 0.01 | 0.1 ± 0.03 | 0.250 |

US 9,844,514 B2

METHODS FOR TREATING AN ESTABLISHED MYOCARDIAL INFARCTION

CROSS-REFERENCE TO RELATED APPLICATION

This application is a continuation-in-part of U.S. patent application Ser. No. 14/348,584, which is the U.S. National Stage (entered 28 Mar. 2014) of International Application No. PCT/US2012/058378, filed 1 Oct. 2012, which claims priority to U.S. Provisional Application No. 61/542,105, filed Sep. 30, 2011. The present application further claims priority to U.S. Provisional Application No. 61/844,267, entitled "Methods for Treating an Established Myocardial Infarction," filed 9 Jul. 2013. The entire disclosures of each of the above applications are hereby incorporated by reference.

GOVERNMENT LICENSE RIGHTS

This invention was made with government support under grant number EB007556 awarded by the National Institutes of Health. The government has certain rights in the invention.

TECHNICAL FIELD

The presently-disclosed subject matter relates to methods for treating an established myocardial infarction. In particular, the presently-disclosed subject matter relates to methods for treating an established myocardial infarction whereby a stromal vascular fraction construct is applied to the site of an established myocardial infarction in a subject.

BACKGROUND

Cardiac disease, including coronary heart disease (CHD) and associated heart failure following myocardial infarction (MI) comprises the most direct and indirect costs of major cardiovascular diseases [1]. Since the innate ability of the heart to repair itself following a MI is largely limited, regenerative therapies for patients with acute MI are being investigated as a means to reduce the extent of ischemic damage, whether as a novel treatment or a supplement to current therapies, such as primary percutaneous coronary intervention and thrombolytic therapy [2].

To successfully intervene in the heart's progressive functional decline with CHD, and specifically MI, there has been a large growth in clinical trials devoted to treat acute and chronic CHD. Multiple Phase II clinical trials, such as the TIME (NCT00684021) and LateTIME (NCT00684060) trials, have recently been conducted to help determine the appropriate timing of cell-based therapy to improve ventricular function and structure post-MI [3]. Specifically, the LateTIME trial was to evaluate the efficacy of cell treatment 2-3 weeks following initial MI in an effort to address high-risk patients with persistent LV dysfunction [3]. This has prompted the need to evaluate the efficacy of successful acute MI cellular therapies in a more clinically challenging model of established or chronic ventricular dysfunction.

Currently, there are many options as to which cell populations are under consideration for treatment of CHD. Of interest, adipose tissue houses an easily isolatable, regenerative, and multipotent cell population defined as the stromal vascular fraction (SVF), consisting of endothelial cells, smooth muscle cells, blood cells and mesenchymal cells containing perivascular and adventitial cells [4,5]. The broad clinical potential of SVF has significantly boosted the number of ongoing clinical trials utilizing adipose-derived cells as a cell therapy [6]. It is worth noting, though, most cell-based therapies are limited by the lack of retention of cells into the target tissue. In fact, one study found that only about 1.3-2.6% of transplanted cells could be detected in the infarcted myocardium in as little as 50-75 minutes after intracoronary injection [7]. However, by changing the delivery method to a cell-laden sheet (implanted onto the epicardium), greater post-infarct survival and greater cell engraftment has resulted compared to intramyocardial injections of the same cells [8]. Furthermore, others have shown that an epicardial cell sheet [8] can be implanted as long as 30 days post-MI and still result in improved angiogenesis and cell survival [9].

BRIEF SUMMARY

Described herein are embodiments including a method of treating an established myocardial infarction, comprising: providing a stromal vascular faction construct, the stromal vascular fraction construct including an amount of stromal vascular fraction cells seeded onto a biocompatible substrate; and applying the stromal vascular fraction construct to the site of the established myocardial infarction in a subject. In another embodiment, the above method increases the amount of perfused vessels at the site of the established myocardial infarction.

Various additional embodiments, including additions and modifications to the above embodiments, are described herein or would be apparent to a person working in this field.

BRIEF DESCRIPTION OF THE DRAWINGS

The accompanying drawings, which are incorporated into this specification, illustrate one or more embodiments of the inventions disclosed herein, together with the detailed description. The drawings are illustrative only, and that what is depicted therein may be adapted based on the text of the specification or the common knowledge within this field.

In the drawings:

FIG. 1A is a plot representing single PV loop recordings during baseline. All MI hearts display a rightward shift in PV relationship compared to the representative control PV loop. FIG. 1B is a table summarizing cardiac functional parameters during PV loop recordings and respective ANOVA p-values. Emax was significantly higher for MI SVF than either the MI or MI VICRYL® polyglactin 910 mesh groups. The asterisk (*) indicates significantly different than MI SVF.

FIG. 2A is an $^{18}$F-FDG PET scan showing an uptake defect in partitioned polar maps in all groups [anterior (top), lateral (right), apex (center)].

FIG. 3A is set of representative photographs of explanted hearts.

FIG. 4A is a set of representative photographs of GS-1+ staining indicating coronary vascular density in the infarct and peri-infarct region. Scale bar=20 μm.

FIG. 5A is a set of representative merged images of IHC staining for dextran$^+$ and αSMC-actin$^+$ in MI (top, left), MI SVF (top, right), and MI VICRYL® brand polyglactin 910 mesh (bottom, left). MI SVF demonstrates more perfused vessels (white arrows) compared to both MI and MI VICRYL® brand polyglactin 910 mesh hearts. Scale bar=20 μm.

FIG. 6A-G show cumulative data comparing MI SVF with the time point of intervention, MI 2 wk. On several parameters, MI SVF hearts maintain similar cardiac function and vascular dynamics as the MI 2 wk group. FIG. 6A is a plot of representative PV loops showing both the lack of rightward shift (vs. MI 2 wk) or reversal of dysfunction (vs. control) for MI SVF. FIG. 6B is a table containing a summary of cardiac functional parameters as assessed by PV loops. FIG. 6C is a set of two $^{18}$F-FDG uptake PET polar map views. FIG. 6D is a chart showing percent relative infarct volume from PET data. FIG. 6E is a set of photographs showing GS-1+ vessel density (Top) and IHC staining showing perfused vessels (Bottom). Scale bar=20 μm. FIG. 6F is a chart showing that MI SVF had significantly higher count of GS-1+ vessel density in the area of infarct than MI 2 wk. FIG. 6G is a chart displaying percent perfused vessels in the area of infarct.

DETAILED DESCRIPTION

Figure 1C:
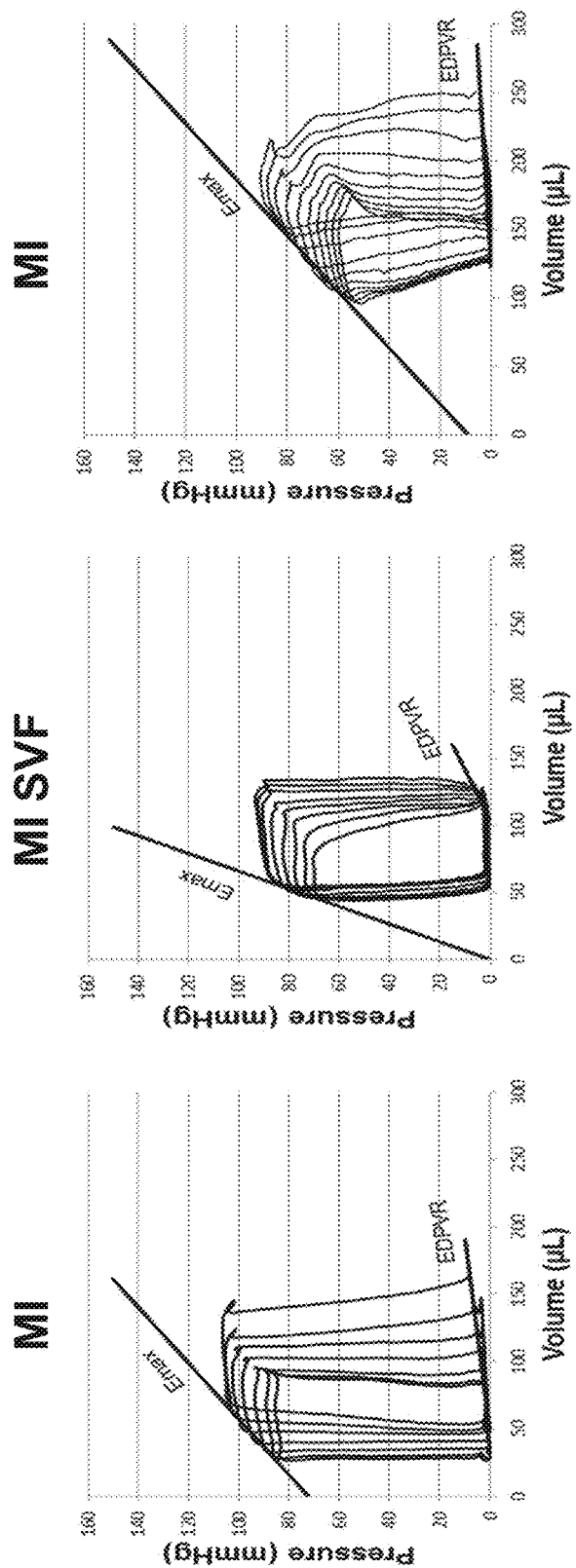
FIG. 1C is a set of graphs showing representative PV loops obtained at different preloads, showing differences in the end-systolic PV relationship (ESPVR, or Emax) between MI (left), MI SVF (center) and MI VICRYL® brand polyglactin 910 mesh (right). The less steep Emax in the MI and MI VICRYL® brand polyglactin 910 mesh loops indicate decreased systolic performance.

Various example embodiments of the present inventions are described herein. The following detailed description is illustrative only and is not intended to be in any way limiting. Other embodiments will readily suggest themselves to such skilled persons having the benefit of this disclosure.

In the interest of clarity, not all of the routine features of the implementations described herein are shown and described. In the development of any such actual implementation, numerous implementation-specific decisions must be made in order to achieve the developer's specific goals, such as compliance with application, safety, regulatory, and business constraints, and that these specific goals will vary from one implementation to another and from one developer to another. Moreover, such a development effort might be complex and time-consuming, but would nevertheless be a routine undertaking of engineering for those of ordinary skill in the art having the benefit of this disclosure.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Through the implantation of a stromal vascular fraction (SVF) construct after a myocardial infarction (MI) and onto an established MI or, in other words, onto a MI during the weeks to months following a MI where cellular necrosis, the beginning of scar tissue formation, and thinning of outer LV wall occurs, it has been surprisingly found that the cell-based intervention provided by applying the SVF construct onto an established infarct halts further deterioration of left ventricular (LV) function compared to untreated hearts, and that this is accomplished, at least in part, through an increase in coronary neovascularization and perfusion, as well as a retention of implanted regenerative cells in the area of infarct. The presently-disclosed subject matter thus includes methods for treating an established myocardial infarction and, in particular, methods for treating an established myocardial infarction whereby a stromal vascular fraction construct is applied to the site of an established myocardial infarction in a subject.

In some embodiments of the presently-disclosed subject matter, a method of treating an established myocardial infarction is provided that comprises the steps of: providing a stromal vascular fraction construct, the stromal vascular fraction construct including an amount of stromal vascular fraction cells seeded onto a biocompatible substrate; and applying the stromal vascular fraction construct to the site of the established myocardial infarction in a subject. In some embodiments, the stromal vascular fraction construct can be applied to the site of the established myocardial infarction at a time period of about 2 weeks to about 6 weeks following a myocardial infarction in the subject to thereby treat the established myocardial infarction. In some embodiments, applying the stromal vascular fraction construct to the site of the established myocardial infarction comprises suturing the stromal vascular fraction construct to an epicardial surface of the heart of the subject.

As used herein, the terms "treatment" or "treating" relate to any treatment of an established myocardial infarction, including but not limited to prophylactic treatment and therapeutic treatment. As such, the terms "treatment" or "treating" include, but are not limited to: preventing an established myocardial infarction or the development of an established myocardial infarction; inhibiting the progression of an established myocardial infarction; arresting or preventing the further development of an established myocardial infarction; reducing the severity of a blood vessel disease; ameliorating or relieving symptoms associated with an established myocardial infarction; and causing a regression of an established myocardial infarction or one or more of the symptoms associated with an established myocardial infarction.

In some embodiments of the presently-disclosed therapeutic methods, applying the stromal vascular fraction construct decreases an amount of fibrosis at the site of the established myocardial infarction. In some embodiments, applying the stromal vascular fraction construct increases an amount of perfused vessels at the site of the established myocardial infarction. In further embodiments, applying the stromal vascular fraction construct reduces an amount of myocardial cell death at the site of the established myocardial infarction.

In yet further embodiments of the therapeutic methods described herein, applying the stromal vascular fraction construct increases an amount of growth factors at the site of the established myocardial infarction. In some embodiments, the growth factors are selected from the group consisting of vascular endothelial growth factor, transforming growth factor-beta 1, placental growth factor, and basic fibroblast growth factor. In some embodiments, the growth factor is vascular endothelial growth factor (VEGF).

With respect to the stromal vascular fraction constructs of the presently-disclosed subject matter, the stromal vascular fraction used in the constructs are those that are typically obtained by enzymatically digesting an amount of adipose tissue obtained from a subject, followed by a period of centrifugation to pellet the stromal vascular fraction of the adipose tissue. In this regard, the stromal vascular fraction contains a number of cell types, including preadipocytes, mesenchymal stem cells (MSCs), endothelial progenitor cells, T cells, B cells, mast cells, and adipose tissue macrophages, as well as small blood vessels or microvascular fragments found within the stromal vascular fraction. For further explanation and guidance regarding the disassociation of adipose tissue to produce a stromal vascular fraction, see, e.g., U.S. Pat. No. 4,820,626, the entire contents of which are incorporated herein by this reference.

The substrates used in connection with the stromal vascular fraction construct can be comprised of a number of materials, but are generally comprised of biocompatible materials that will not have a long-lasting inflammatory or other adverse effects when placed in the body of a subject. In some embodiments, the biocompatible substrate comprises a VICRYL® brand polyglactin 910 mesh.

As used herein, the term "subject" includes both human and animal subjects. Thus, veterinary therapeutic uses are provided in accordance with the presently disclosed subject matter. As such, the presently-disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See, e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Polynucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples.

EXAMPLES

Material and Methods for Examples 1 to 7

Animal Surgeries.

All animal surgeries were performed in accordance with protocols approved by the University of Louisville animal review committee and the Guide for the Care and Use of Laboratory Animals published by the US National Institutes of Health (NIH Publication, 9th Edition, 2011). In all animal surgeries, adequate anesthesia was maintained by monitoring lack of tactile toe pinch reflex, heart rate and/or respiration.

Stromal Vascular Fraction Isolation.

Green fluorescent protein (GFP)-tagged adult male Fischer-344 rats (Rat Research and Resource Center, University of Missouri, Columbia, Mo.) were put under anesthesia (Ketamine 40-80 mg/kg and Xylazine 5-10 mg/kg). GFP+ SVF cells were isolated from epididymal fat pads. Cervical dislocation was used to euthanize the rats. Harvested fat pads were washed in 0.1% Bovine Serum Albumin in Phosphate Buffered Saline (BSA-PBS), finely minced and digested in 2 mg/ml Type I collagenase solution for 40 min at 37° C. with vigorous shaking Buoyant adipocytes were removed by centrifugation and the entire cell pellet suspended in 0.1% BSA-PBS. Cells were immediately plated ($1 \times 10^6$ cells/cm$^2$) onto a piece of VICRYL® brand polyglactin 910 mesh. 1×1.5 cm, and cultured for 14 days in Dulbecco's Modified Eagle's Medium (DMEM) with 10% FBS.

Myocardial Infarction.

After anesthesia was introduced (Isoflurane 1-3%-$O_2$ balance), the MI was performed as described previously [10]. Briefly, infarcts were performed by left anterior descending (LAD) artery ligation with 7-0 silk suture (Ethicon) and confirmed via visualization of blanched tissue distal to the ligation site. The rat was allowed to recover and given Buprinorphine (0.05 mg/kg, SQ) every 8-12 hrs for the next 48 hrs.

Study Design and Construct Implantation.

Table 1 illustrates the study design of the four experimental groups used in the study. Infarcted animals were immediately randomized into one of 4 groups (n=9/group). Two groups were left untreated until explant, 2 Week MI (MI 2 wk) and 6 Week MI (MI). Two weeks following the initial MI surgery, rats in the treated groups were assigned to either the SVF (MI SVF) or VICRYL® brand polyglactin 910 mesh (MI VICRYL® brand polyglactin 910 mesh) group. Rats were surgically prepared as described in MI section and the procedure was performed as described previously [10]. Briefly, the SVF construct or VICRYL® brand polyglactin 910 mesh mesh without cells was laid onto the epicardium, covering the area of infarct and overlapping slightly into the proximal non-infarct region. A single 7-0 silk suture was sewn immediately distal to the LAD occlusion to secure the construct to the epicardial surface, and rats were allowed to recover as described above for 4 weeks.

TABLE 1

Study design of all experimental groups.

| Groups | 0 weeks | 2 weeks | 6 weeks |
|---|---|---|---|
| MI 2 wk | LAD ligation | Explant "MI 2 wk" | |
| MI | LAD ligation | | Explant "MI" |
| MI SVF | LAD ligation | Implant SVF | Explant "MI SVF" |
| MI VICRYL® polyglactin 910 brand mesh | LAD ligation | Implant VICRYL® polyglactin 910 brand mesh | Explant "MI VICRYL® brand polyglactin 910 brand mesh" |

The MI 2 wk group was included to compare the SVF treated group to the time point of intervention. The VICRYL® brand polyglactin 910 mesh alone implant group was included as an epicardial implant control. All endpoint parameters were assessed at 2 weeks or 6 weeks following initial MI. Rats were euthanized by removal of the heart.

Left Ventricular Function Assessment.

PV loop relationships of the LV utilized the Millar conductance system and were performed according to our published methods [12]. Briefly, after receiving an injection of anesthesia (Ketamine 40-80 mg/kg and Xylazine 5-10 mg/kg), a substernal transverse incision to expose the inferior vena cava (IVC) was performed. An apical stab was used for catheter insertion, and the catheter was positioned along the cardiac longitudinal axis with the distal electrode in the aortic root and the proximal electrode in the LV apex. Placement of the catheter was monitored directly. Overall LV function was assessed under baseline conditions, following transient inferior vena cava (IVC) occlusion (to assess contractility and LV stiffness), and after intravenous administration of 20-40 ul of 30% saline (for conductance volume calibration). Parameters assessed included heart rate (HR), cardiac output (CO), end systolic and diastolic pressure (ESP and EDP), end systolic and diastolic volume (ESV and EDV), stroke volume (SV), ejection fraction (EF), and maximal slope of systolic pressure increment (+dP/dT) and diastolic pressure decrement (−dP/dT). Emax (end systolic PV relationship, or ESPVR) and end diastolic PV relationship (EDPVR) slopes were calculated by linear regression of the loops during IVC occlusion.

PET Imaging.

The most widely used and validated PET radiotracer for the assessment of myocardial glucose utilization and metabolically active tissue is $^{18}$F-FDG [13]. Each rat was injected with a dose of $^{18}$F-FDG (28-44 MBq×0.6 ml saline) via the lateral tail veins. Thirty to forty-five minutes after the $^{18}$F-FDG IV injection, each rat was anesthetized with isoflurane (1-3%) and securely taped onto the imaging bed of a Siemens R4 MicroPET (Knoxville, Tenn.). A 17-partitioned polar cardiac map was produced for each rat. Imaging data was analyzed with the Siemens Inveon Imaging system. Reduced uptake regions (<70% of the maximum uptake) were calculated by summing the individual volumes (in $mm^3$) from each reduced $^{18}$F-FDG uptake region. Total left ventricle (LV) volume was calculated by summing the individual volumes from all short axis slices. The extension of infarction was compared between animals using the equation:

% Relative Infarcted Volume=(Infarcted myocardial volume/Total LV volume)×100

Histology.

Rats received an injection of anesthesia (Ketamine 40-80 mg/kg and Xylazine 5-10 mg/kg) and then were perfused with dextran (Tetramethylrhodamine, Molecular Probes) at 2 mg/ml via the jugular vein (circulating 15') before hearts were explanted. General histological structure of the heart was determined using an ultramicrotome (Leica) approximately 2 mm proximal to the apex, ~15 μm thick sections. A subset of sections was stained using Masson's Trichrome protocol and infarct regions were manually traced as previously described [10]. Vascular characteristics were identified from infarcted regions (approximately 1 mm proximal to the apex on free wall of LV). Vascular endothelial cells (indicative of total vessel density) were identified using a rodent-specific lectin, GS-1 (*Griffonia simplicifolia* I, 1:250). On separate slides, perfused vessels were identified by counting dextran$^+$ vessels while vascular smooth muscle cells were identified using alpha-smooth muscle actin$^+$ staining (αSMC-actin, 1:100). Total vessels in these slides were calculated by counting positive dextran or αSMC-actin staining, then subtracting vessels positive for both markers (overlap). Percent perfusion was calculated by counting [dextran$^+$/(total vessels)]×100. In each animal, 5 discrete, random images (20× magnification) from the infarct region or area at risk were analyzed for total vessel density and % perfused vessels.

Statistical Analysis.

Mean differences between groups in all PV loop parameters, PET infarct volume calculations, infarct size, and vessel counts were determined by one-way ANOVA calculation, with post-hoc analysis determined by Tukey's test, P=0.05.

Example 1

Impact of Construct Implantation on Overall Heart Function

To determine if the SVF construct impacted overall LV function compared to other MI groups, PV relationships were acquired. The PV relationship was shifted to the right in MI and MI VICRYL® brand polyglactin 910 mesh animals, due mainly to an increase in both ESV and EDV compared to MI SVF (though these failed to reach significance, ANOVA ESV p=0.09, EDV p=0.14, FIG. 1A,B). A representative sham "control" PV loop is included to illustrate the rightward shift of all MI groups. There were no significant differences between groups in hemodynamic parameters at rest, such as HR, CO, ESP, EDP, EF, SV, +/−dP/dt, and EDPVR slope (FIG. 1B).

FIG. 1C displays representative PV loops obtained during IVC occlusion in MI, MI SVF, and MI VICRYL® brand polyglactin 910 mesh hearts. Indices of contractility and LV stiffness were calculated (slope of ESPVR [Emax] and EDPVR) and are displayed in FIG. 1B,C. The Emax slopes during IVC occlusion were significantly less steep in the MI and MI VICRYL® brand polyglactin 910 mesh groups compared to MI SVF (MI vs. MI SVF p=0.005, MI SVF vs MI VICRYL® brand polyglactin 910 mesh p=0.002), indicating decreased systolic performance and contractile function. Chronic changes in Emax from CHD can also give us insight into changes in cardiac morphometry, such as hypertrophy and fibrosis, and is considered a more complex indicator of "contractility" [14]. Pacher et al. (2004) reported Emax slope values of 2.6±0.2 for normal male Fischer-344 rats [15], so it is important to note that treatment with the SVF construct 2 weeks post-MI did not reverse cardiac dysfunction back to normal/sham levels.

Example 2

Figure 2B:
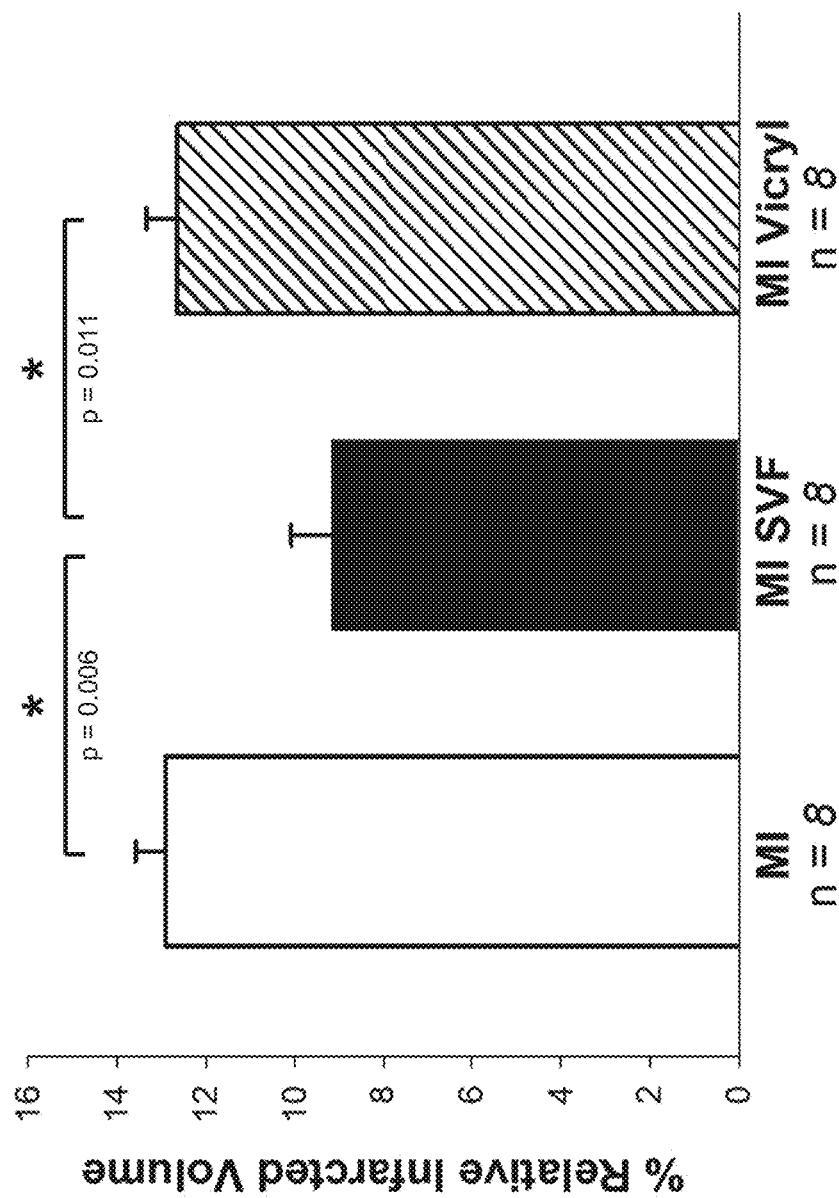
FIG. 2B is a chart showing that relative infarcted volume, calculated as a ratio of infarcted volume (regions with $^{18}$F-FDG uptake<70%) to total LV volume, was significantly higher in the MI and MI VICRYL® brand polyglactin 910 mesh groups compared to MI SVF.

Assessment of Myocardial Viability $^{18}$F-FDG PET is considered the most sensitive means to assess myocardial viability compared to any other imaging modality [16]. Myocardial glucose utilization (indicative of metabolism) measured by $^{18}$F-FDG uptake demonstrated the ischemic injury in the anterior wall of infarcted rats in the representative polar maps (FIG. 2A). To compare the relative myocardial volume that was defined as infarcted (<70% maximum $^{18}$F-FDG uptake), percent relative infarcted volume was calculated in each group. Percent relative infarcted volume was significantly increased in MI and MI VICRYL® brand polyglactin 910 mesh compared to MI SVF hearts (MI: 12.9±0.7, MI VICRYL® brand polyglactin 910 mesh: 12.6±0.7, MI SVF: 9.1±0.9, FIG. 2B).

Example 3

Heart Remodeling and Fibrosis Following Post-MI Intervention

To corroborate infarct volume analysis by in vivo PET imaging, histologic evaluation of hearts using Masson's Trichrome analysis was performed. As expected, the MI and MI VICRYL® brand polyglactin 910 mesh group exhibited more percent collagen and fibrosis in the LV than the MI SVF group (MI: 47±5, MI VICRYL® brand polyglactin 910 mesh: 38±4, MI SVF: 24±3, FIG. 3C), though the post-hoc analyses between MI VICRYL® brand polyglactin 910 mesh and MI SVF failed to reach significance (p=0.074).

Example 4

Vessel Characteristics in the Area of Infarct

Figure 4B:
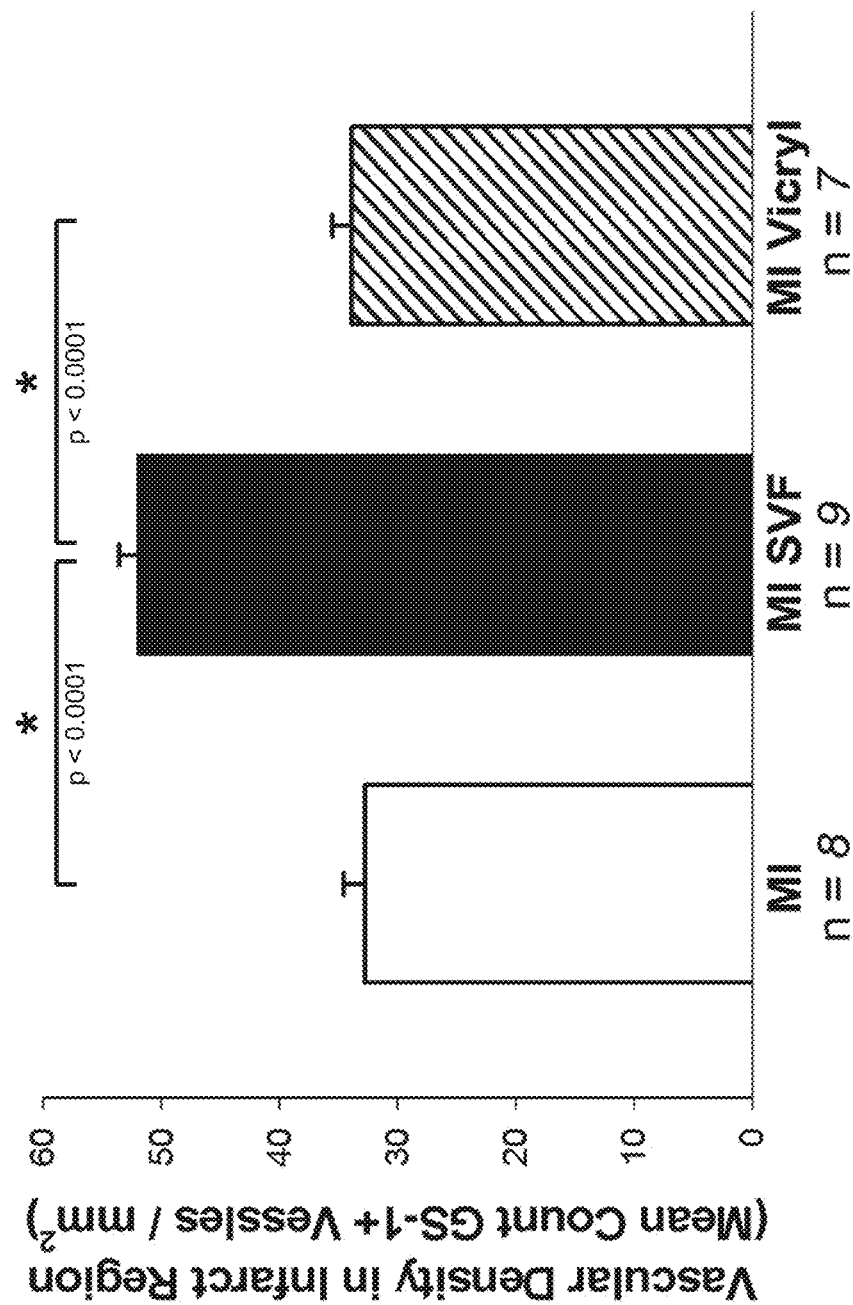
FIG. 4B is a chart showing how the example MI SVF group exhibited significantly more GS-1+ vessels in the area of infarct when compared to both the MI and MI VICRYL® brand polyglactin 910 mesh groups.

Total vessel count in the area of infarct was determined through GS-1+ staining Both MI and MI VICRYL® brand polyglactin 910 mesh exhibited less vascular density in the infarct region compared to the MI SVF (FIG. 4). Since previous data indicate that vascular density does not imply vascular perfusion [10], we also evaluated vessel perfusion through dextran perfusion prior to explant. When treated with the SVF construct at 2 weeks post-MI, there were significantly more perfused vessels in the area of infarct compared to both MI and MI VICRYL® brand polyglactin 910 mesh hearts (MI SVF: 59±5, MI: 43±4, MI VICRYL® brand polyglactin 910 mesh: 41±7, FIG. 5D).

Example 5

SVF Construct and Time Point of Intervention

Figure 6A:
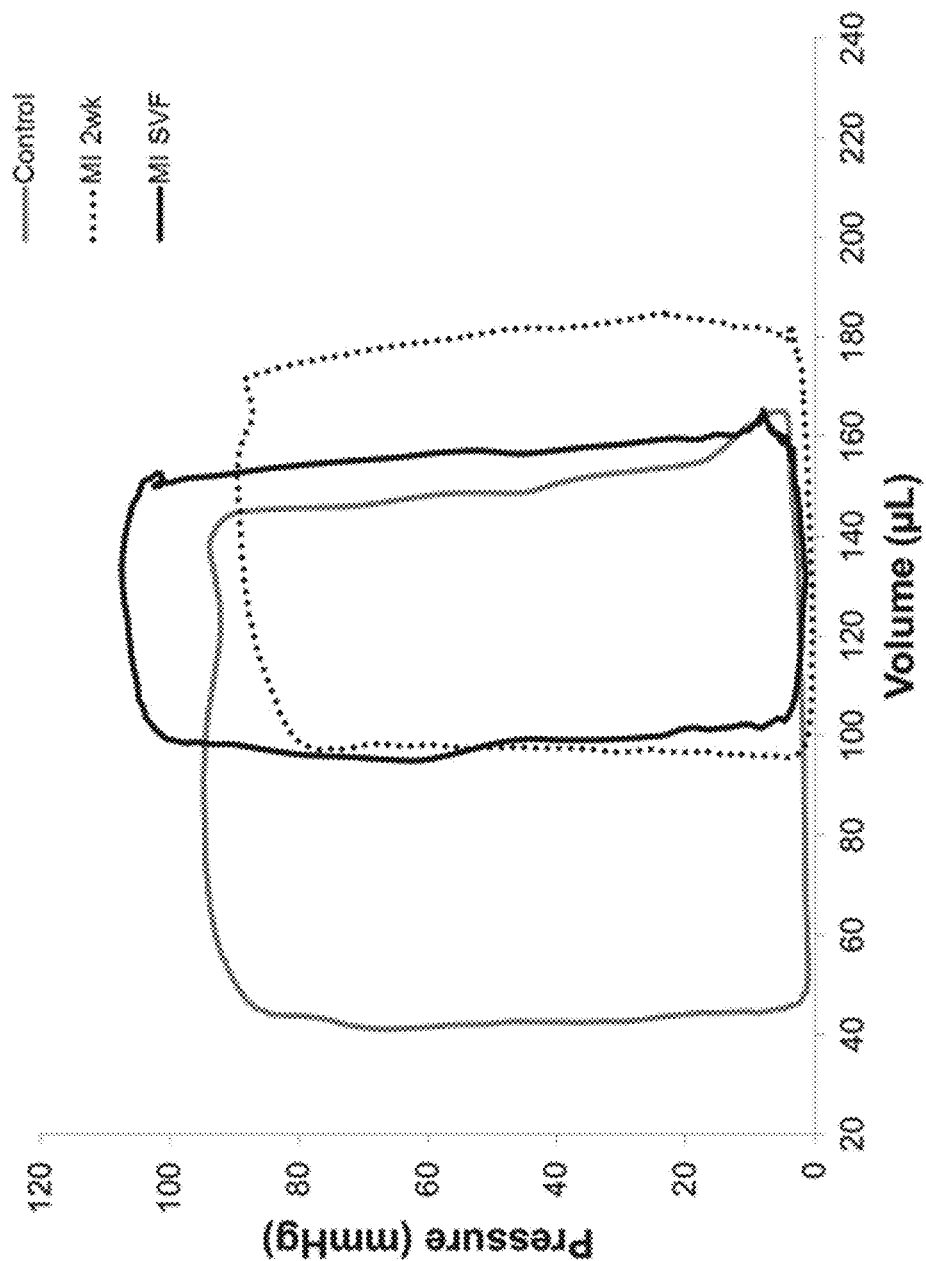
Figure 6C:
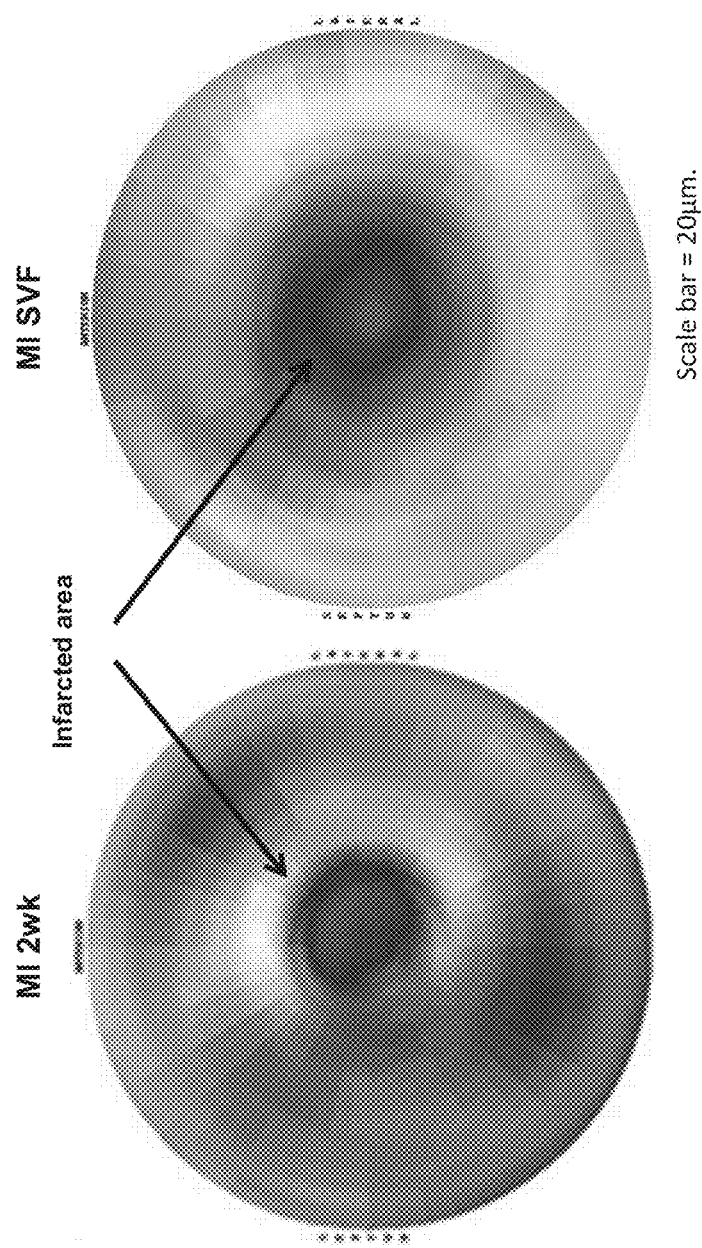
Figure 6D:
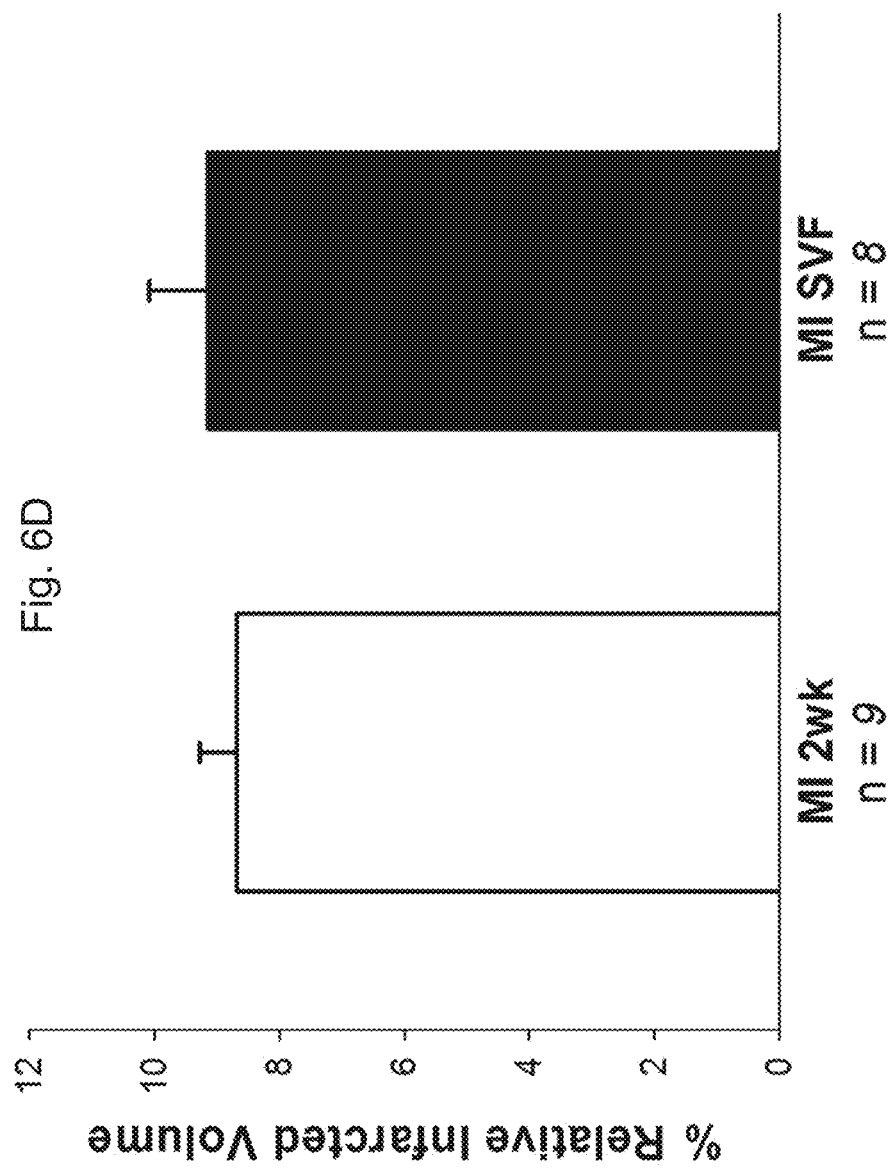
Figure 6E:
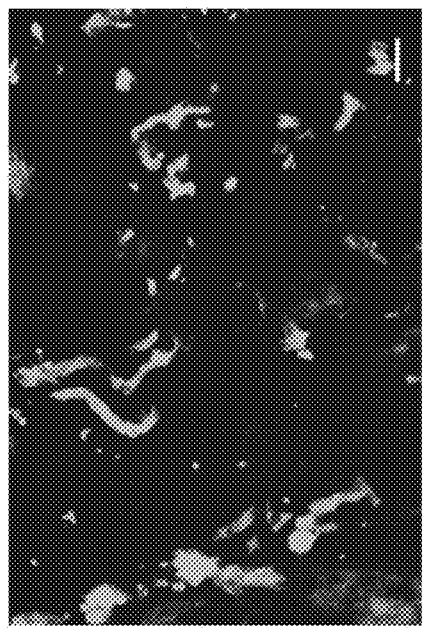
Figure 6E:
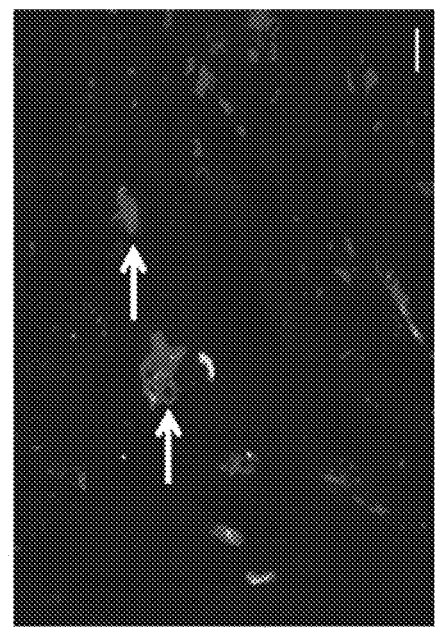
Figure 6E:
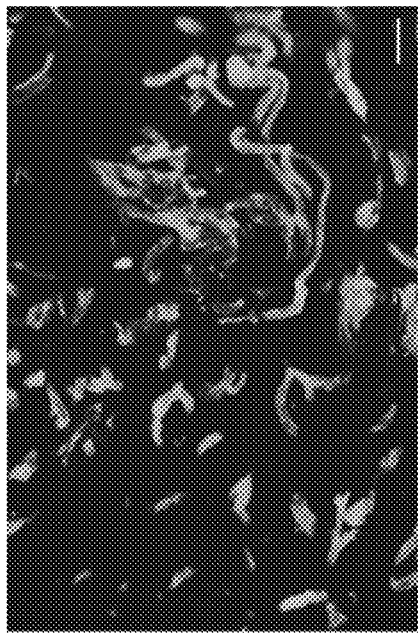
Figure 6E:
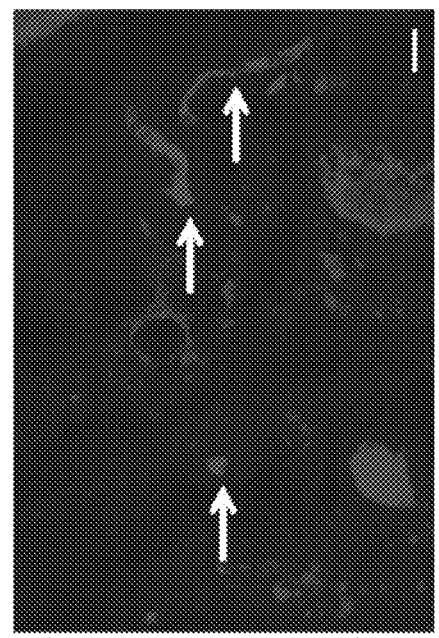

The current results support the hypothesis that the SVF construct acts to preserve or halt ventricular dysfunction at the time of implant, as there were no significant differences in hemodynamic parameters assessed via PV loops between the time point of intervention, MI 2 wk, and MI SVF (FIG. 6A,B). There were no significant differences in $^{18}$F-FDG % relative infarcted volume between MI SVF and MI 2 wk (FIG. 6C,D) or in Masson's Trichrome % infarct (data not shown). Compared to the time point of intervention (MI 2 wk), the infarct area in MI SVF exhibited greater vascular density (FIG. 6E,F), but there was no difference in the % of perfused vessels between these groups (FIG. 6E,G).

Example 6

SVF Cell Engraftment

Four weeks after SVF construct implantation, IHC staining did not reveal the presence of engrafted GFP+ SVF elements in the area of infarct (data not shown). In order to further evaluate the possibility of GFP+ cells that may not be identified through IHC, PCR amplification of the GFP gene was performed on LV tissue from MI SVF. Confirming IHC results, the GFP gene was not amplified in samples from MI SVF (data not shown).

Example 7

Vascular Endothelial Growth Factor (VEGF) Production

To determine the amount of VEGF produced by the SVF construct, media was sampled from wells of individual SVF constructs following 4 days of culture. Using ELISA Kit for VEGF (Invitrogen), media without an SVF construct was 5 pg/mL. Average VEGF from n=7 SVF constructs was 8434±454 pg/mL (data not shown).

Discussion of Examples 1 to 7

The above examples illustrate, among other things, that regenerative medicine therapy previously shown to preserve myocardial function following MI can restore and/or maintain function if applied at a later time point. The primary findings from this study are: 1) clinical indices of heart function, such as Emax (indicative of systolic performance and contractile function) and PET imaging of cardiac viability, established that treatment with the SVF construct at 2 weeks post-MI halted the progressive worsening of LV function displayed by untreated and control MI hearts (MI and MI VICRYL® brand polyglactin 910 mesh), and 2) hearts treated with an SVF construct exhibited an increase in both total and perfused vessels in the infarcted area compared to MI and MI VICRYL® brand polyglactin 910 mesh. These data, coupled with the similarities between the time of intervention and the end-point of the treated group (MI 2 wk and MI SVF, FIG. 6), indicate that the SVF construct implanted onto an established infarct prevented or halted worsening of cardiac function and targeted coronary vascular perfusion in the infarct region allowing sustained coronary viability.

A major barrier to the efficacy of regenerative medicine in a given tissue is the method of delivery of the selected cell population. The volume of cells that remain in the heart, delivered either by direct injection into the myocardium or through intracoronary infusion, can be <10% hours after transplantation [7,17]. Catheter-based injectable materials offer an alternative solution to delivering cells directly to the infarcted area while simultaneously facing the need for a longer-lasting cell-matrix platform and interaction within the myocardium; however, it is less clear if injectable gels laden with cells would be able to withstand (and survive) the mechanical load of a contracting myocardium after injection [18]. Fortunately, tissue engineers have propelled the efficacy of cell retention by developing cell sheets that can be implanted into/onto a particular tissue [8,19]. Direct comparisons between direct injections (in-scar myocardial) and an epicardial tri-layered cell-sheet implant resulted in higher rates of post-infarction survival in rats and greater numbers of engrafted cells in the hearts treated with a cell sheet [8]. A cell-laden patch is a very effective delivery method to improve cell retention post-implant [10,12,20].

While transplanted cells have multiple modes of action in damaged myocardial tissue, the leading mechanism of action put forth is by increasing myocardial perfusion, followed by enhancing endogenous cell survival, progenitor homing, and decreasing fibrosis [21]. Important to all of these mechanisms is the potential of SVF-induced paracrine activity. Contrary to our previous results, GFP+ cells were not incorporated into the coronary microvasculature upon explant, yet improvements in functional parameters of the microcirculation were realized through the increase in both total and perfused vessels in hearts treated with the SVF construct. Adipose-derived microvessels [22] and cells [23] have the capability of forming a de novo microvasculature and migrating into the vessel wall of existing neovessel segments to assemble parts of the vasculature; however, this study suggests a likelier mechanism where implantation of the SVF construct following MI promotes a positive neovascularizing environment. In fact, media collected from the SVF construct prior to implant exhibited high amounts of VEGF (8434±454 pg/mL), which is approximately 7× the amount of VEGF produced by similar 3-dimensional (3D) constructs laden with human dermal fibroblasts (~1000 pg/mL [24] and 1600 pg/mL [25]).

Cultured SVF isolated from human lipoaspirate has previously been shown to produce high levels of VEGF [26]. In addition to VEGF, adipose-derived stem cells can also produce large amounts of transforming growth factor $\beta_1$(TGF $\beta_1$), placental growth factor, and basic fibroblast growth (FGF) factor [27], all of which support the impressive angiogenic effects reported previously [10,27,28]. Culturing cells on a 3D construct may alter the relative expression and production of these growth factors and cytokines secreted by SVF, but this is unlikely in our hands. When examining a variety of angiogenic growth factor gene expressions, including VEGF, FGF, HGF, Angiopoietins, PDGFR$_\beta$, Transforming growth factors, and Tnfα, we have shown similar gene expression between flask-cultured SVF and the SVF cultured onto VICRYL® brand polyglactin 910 mesh as used in the present study (data not shown). How long these proangiogenic cytokines remain following implant and which, if not all, are necessary for scar neovascularization and vessel maturation remains open for future exploration.

Figure 3B:
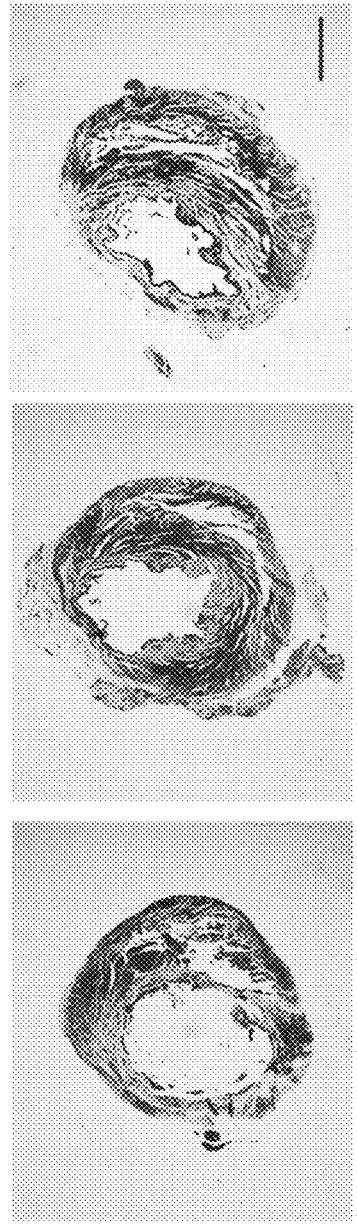
FIG. 3B is a set of representative images of trichrome-stained sections. Scale bar=1 mm.
Figure 3C:
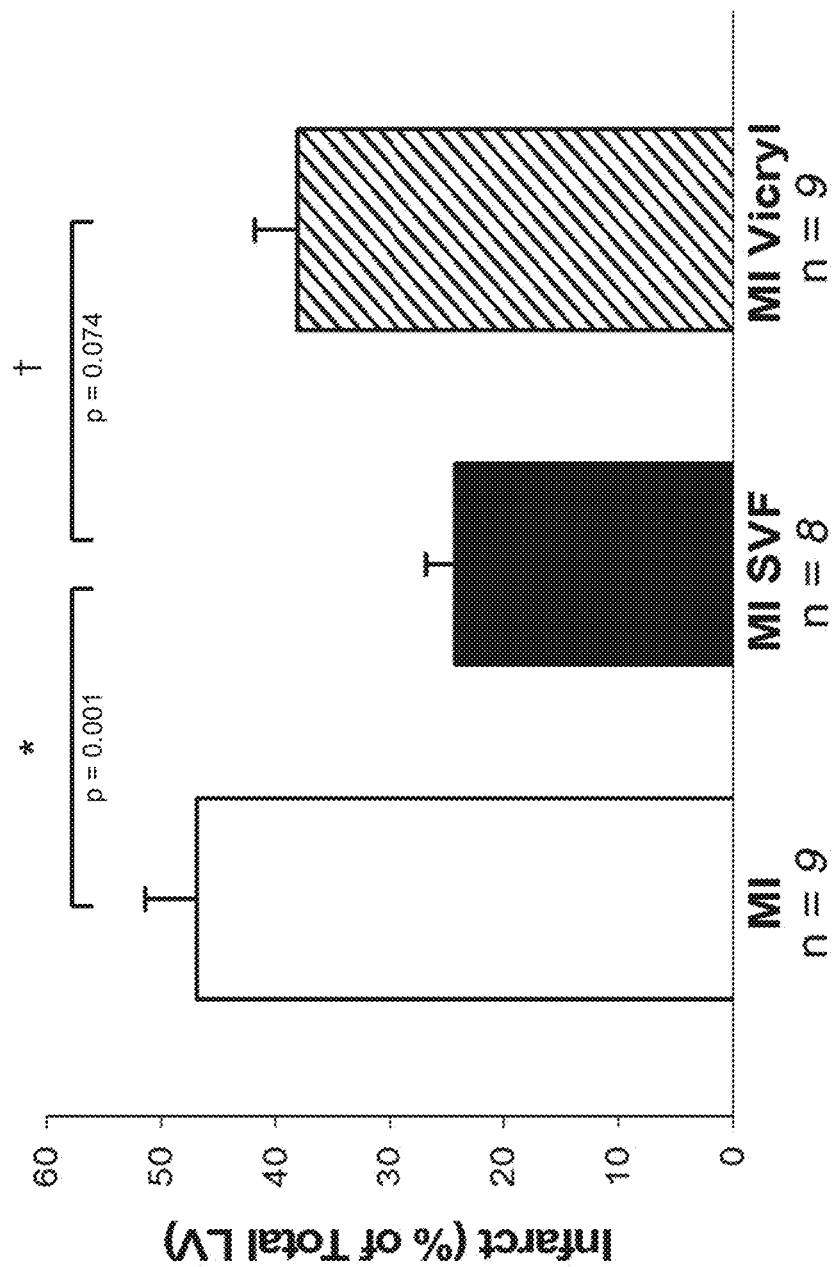
FIG. 3C is a chart showing infarct size as a percentage of total LV per experimental group by trichrome analysis.

Although PET imaging is a well-established modality to evaluate myocardial perfusion, metabolism and viability in the clinical population, it is used significantly less in rodent models of MI [29]. $^{18}$F-FDG is considered the most sensitive means to assess myocardial viability. Following ischemia, the uptake of glucose by the myocardium is increased acutely, but is decreased in areas of very severe ischemia. Clinical trials using bone marrow-derived stem cell (BMSC) intracoronary injection therapy for both acute [30,31] and chronic [32] MI have shown an increased $^{18}$F-FDG uptake in the infarct zone of patients. Direct comparison of $^{18}$F-FDG uptake between hearts treated with either adipose-derived stem cells (ADSC) or BMSC after MI showed ADSC injections resulted in greater sum uptake of $^{18}$F-FDG in all 17 segments of the polar map [33]. The present results support these studies, as the amount of myocardial area with reduced $^{18}$F-FDG uptake was larger in MI and MI VICRYL® brand polyglactin 910 mesh hearts compared to those treated with the SVF construct (FIG. 3B). Furthermore, we believe this is the first study to utilize PET imaging, and specifically $^{18}$F-FDG, as a means to evaluate the functional changes in myocardial viability after MI and adipose cell construct therapy in rats. However, more studies are needed to determine how SVF could potentially contribute to more viable tissue and subsequently, higher metabolic activity in the myocardium, and if that is necessary for the realization of successful post-infarct repair.

Figure 5B:
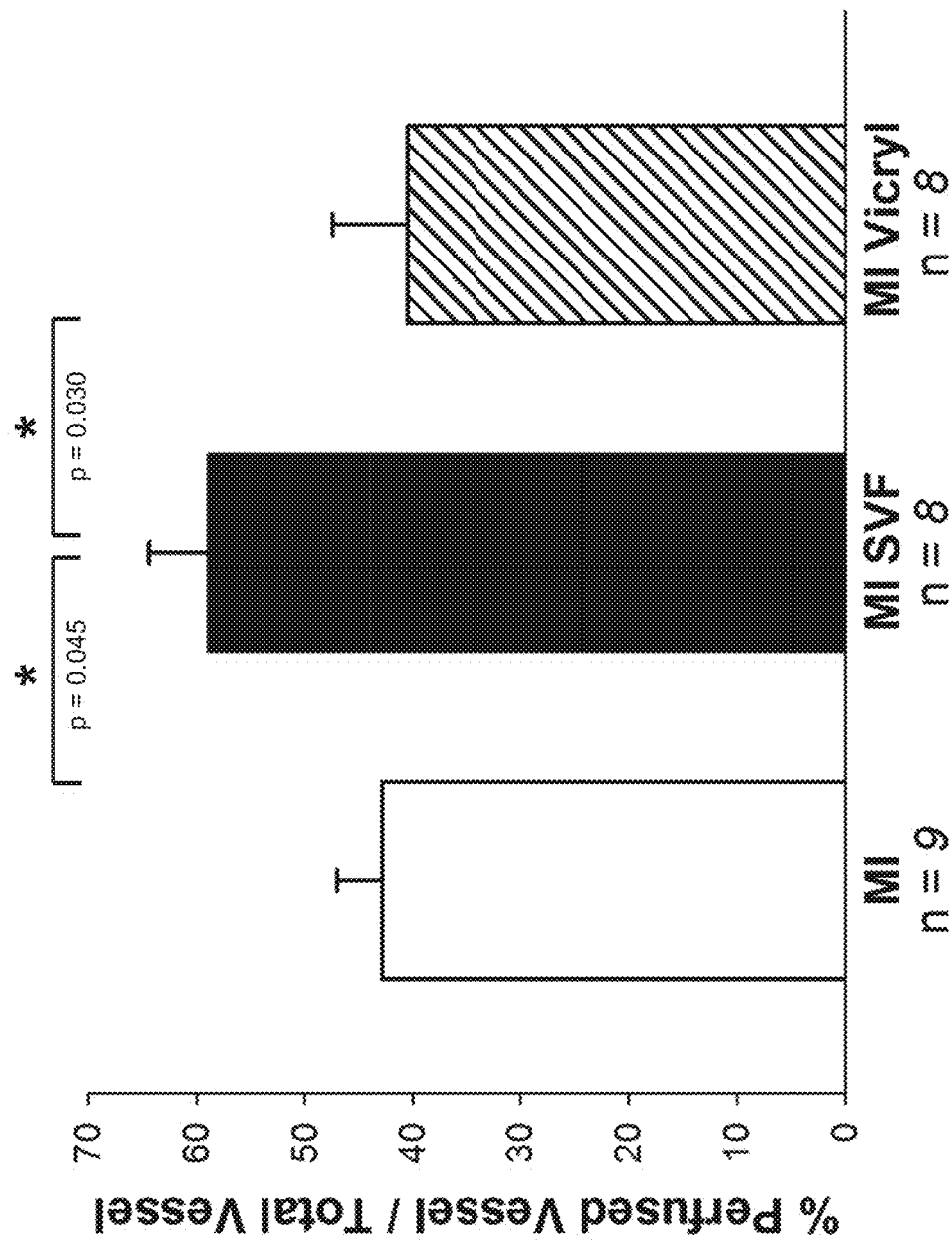
FIG. 5B is a chart showing the percentage of perfused vessels in this example.

Auspicious microcirculatory function is a critical factor in the post-MI repair process and is linked with increased viable myocardium following acute MI [34,35]. The current results support this association, as MI SVF hearts exhibited preserved myocardial viability (FIG. 2) and increased vessel count and perfusion in the at-risk area compared to MI and MI VICRYL® brand polyglactin 910 mesh hearts (FIG. 4,FIG. 5). Multiple studies have shown a similar increase in vessel density (through IHC) in chronic MI hearts after treatment with either BMSC [36] or ADSC [37,38]. Furthermore, a large animal study by Valina et al. (2007) described an increase in both neovascularization and coronary perfusion (through single photon emission computed tomography) in the infarct area after acute MI treatment with either BMSC or ADSC [39]. This concurrent increase in vascular density and perfusion is important to note, because our previous study demonstrated that neovascularization in infarcted regions of the heart does not necessarily translate into improved coronary BF, as only hearts treated with an SVF construct at the time of infarct maintained functional BF reserve in the infarct region compared to untreated hearts [10].

It was recently demonstrated that the SVF construct correlated with preserved heart function and microvascular blood flow in the infarct area when implanted immediately following infarction [10], but it was unknown whether this therapy could impart similar beneficial effects if it was implanted on an established and/or remodeling infarct. In 2006, Miyahara et al. utilized a cultured monolayer of adipose-derived mesenchymal stem cells (MSC) and implanted four weeks after coronary ligation. The MSC sheet, created following 3-5 passages, showed engraftment into the epicardium and progressively thickened the outer LV wall in situ for 28 days until explant [19]. Hamdi et al.

Figure 6F:
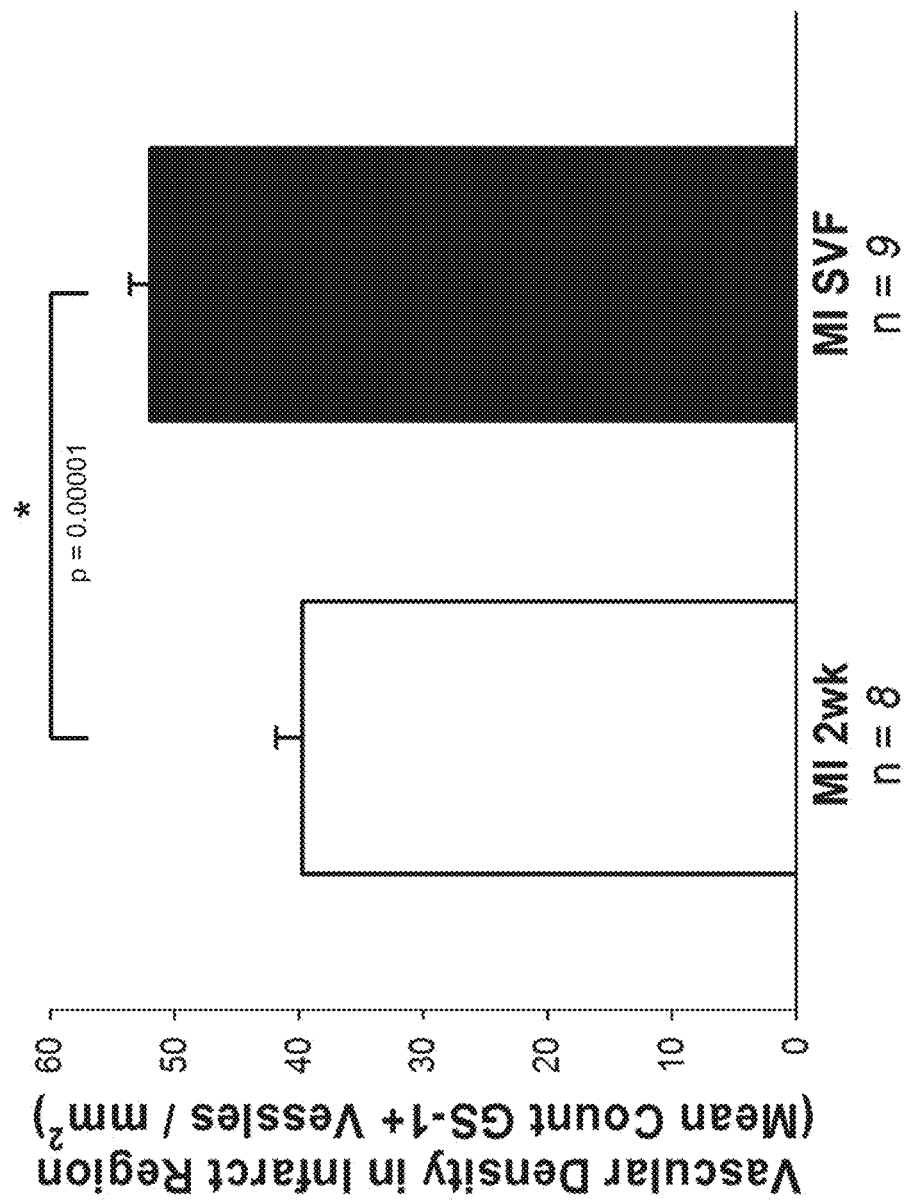
Figure 6G:
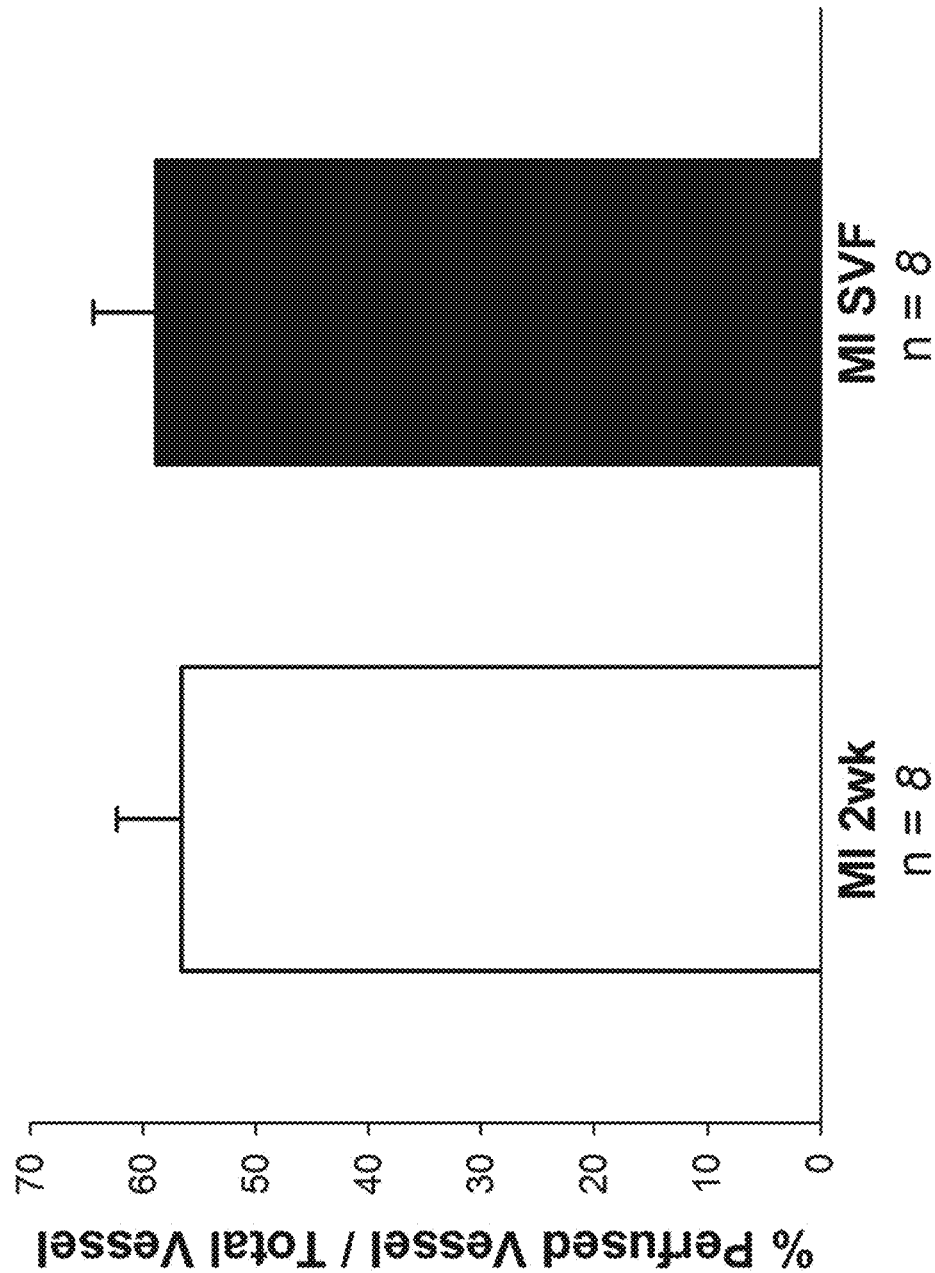

(2011) also utilized a four-week delayed implant of a GFP+ progenitor cell sheet following MI, and successfully identified implanted cells in the infarct region 2 months following implant. However, one major protocol difference that these studies incorporated was a daily immunosuppression injection to suppress host-versus graft reaction mediated by T cells, which can be triggered by GFP [40]. Conversely, we were unable to detect GFP+ cells upon explant in the present study, either through immunohistochemistry or through RNA analysis (data not shown). It should be noted that the present study did not include an immunosuppressive therapy, which may explain why GFP+ cells were not detected 28 days following implant. However, why we were previously able to detect GFP+ SVF cells in acute MI without immunosuppressive therapy is likely because of a time-dependent stage of post-MI inflammation that is particularly specific to transplanted GFP+ cells. Furthermore, at the time point of intervention (MI 2 wk), there are significantly less GS-1+ vessels in the area of infarct than compared to explant after SVF treatment (FIG. 6F). It is possible that in addition to the lack of immunosuppressive therapy in the present study, the acute reduction in coronary vessels at the time point of implant influences the ability of the GFP+ cells to survive and remain in the infarcted area.

Therapeutic treatment with the SVF construct on an established infarct may result in preserved myocardial viability and function, in addition to increased microvascular perfusion in the infarcted area compared to untreated MI hearts in rats. This tissue engineering approach of creating an SVF-laden construct can increase the cell quantity that can be implanted into an ischemic area without massive rates of acute cell death and also improves cell retention over time [18]. The present results indicate that treatment with an SVF construct, either immediately or during the active remodeling phase of scar formation post-MI, halts deteriorating cardiac function and maintains LV viability and microcirculatory perfusion. The clinical potential of an autologous construct made from adipose-derived SVF is high, as the SVF construct may be utilized in conjunction to existing MI therapies to promote microvessel survival and/or growth of new vessels following coronary infarct.

Throughout this application, various references are mentioned. All such references are incorporated herein by reference, including the references set forth in the following list:

REFERENCES

1. Heidenreich P A, Trogdon J G, Khavjou O A, et al. Forecasting the Future of Cardiovascular Disease in the United States: A Policy Statement from the American Heart Association. Circulation. 2011; 123:933-944.
2. Go A S, Mozaffarian D, Roger V L, et al. Heart Disease and Stroke Statistics—2013 Update: A Report from the American Heart Association. Circulation. 2013; 127:e6-e245.
3. Buxton D B, Skarlatos S I. Support for Cardiovascular Cell Therapy Research at the National Heart, Lung, and Blood Institute. Circ. Res. 2012; 110:1549-1555.
4. Zimmerlin L, Donnenberg V S, Pfeifer M E, et al. Stromal Vascular Progenitors in Adult Human Adipose Tissue. Cytometry A.77:22-30.
5. James A W, Zara J N, Zhang X, et al. Perivascular Stem Cells: A Prospectively Purified Mesenchymal Stem Cell Population for Bone Tissue Engineering. Stem cells translational medicine. 2012; 1:510-519.
6. Gir P, Oni G, Brown S A, et al. Human Adipose Stem Cells: Current Clinical Applications. Plast. Reconstr. Surg. 2012; 129:1277-1290.
7. Hofmann M, Wollert K C, Meyer G P, et al. Monitoring of Bone Marrow Cell Homing into the Infarcted Human Myocardium. Circulation. 2005; 111:2198-2202.
8. Hamdi H, Planat-Benard V, Bel A, et al. Epicardial Adipose Stem Cell Sheets Results in Greater Post-Infarction Survival Than Intramyocardial Injections. Cardiovasc. Res. 2011; 91:483-491.
9. Derval N, Barandon L, Dufourcq P, et al. Epicardial Deposition of Endothelial Progenitor and Mesenchymal Stem Cells in a Coated Muscle Patch after Myocardial Infarction in a Murine Model. Eur. J. Cardiothorac. Surg. 2008; 34:248-254.
10. Leblanc A J, Touroo J S, Hoying J B, et al. Adipose Stromal Vascular Fraction Cell Construct Sustains Coronary Microvascular Function after Acute Myocardial Infarction. Am J Physiol Heart Circ Physiol. 2012; 302:H973-982.
11. Cobb F R, Bache R J, Rivas F, et al. Local Effects of Acute Cellular Injury on Regional Myocardial Blood Flow. J. Clin. Invest. 1976; 57:1359-1368.
12. Shepherd B R, Hoying J B, Williams S K. Microvascular Transplantation after Acute Myocardial Infarction. Tissue Eng. 2007; 13:2871-2879.
13. Camici P G, Prasad S K, Rimoldi O E. Stunning, Hibernation, and Assessment of Myocardial Viability. Circulation. 2008; 117:103-114.
14. Pacher P, Nagayama T, Mukhopadhyay P, et al. Measurement of Cardiac Function Using Pressure-Volume Conductance Catheter Technique in Mice and Rats. Nat Protoc. 2008; 3:1422-1434.
15. Pacher P, Mabley J G, Liaudet L, et al. Left Ventricular Pressure-Volume Relationship in a Rat Model of Advanced Aging-Associated Heart Failure. Am J Physiol Heart Circ Physiol. 2004; 287:H2132-2137.
16. Schinkel A F, Bax J J, Poldermans D, et al. Hibernating Myocardium: Diagnosis and Patient Outcomes. Curr. Probl. Cardiol. 2007; 32:375-410.
17. Dow J, Simkhovich B Z, Kedes L, et al. Washout of Transplanted Cells from the Heart: A Potential New Hurdle for Cell Transplantation Therapy. Cardiovasc. Res. 2005; 67:301-307.
18. Eschenhagen T, Eder A, Vollert I, et al. Physiological Aspects of Cardiac Tissue Engineering. Am J Physiol Heart Circ Physiol. 2012; 303:H133-143.
19. Miyahara Y, Nagaya N, Kataoka M, et al. Monolayered Mesenchymal Stem Cells Repair Scarred Myocardium after Myocardial Infarction. Nat. Med. 2006; 12:459-465.
20. Kellar R S, Shepherd B R, Larson D F, et al. Cardiac Patch Constructed from Human Fibroblasts Attenuates Reduction in Cardiac Function after Acute Infarct. Tissue Eng. 2005; 11:1678-1687.
21. Mazo M, Gavira J J, Pelacho B, et al. Adipose-Derived Stem Cells for Myocardial Infarction. J Cardiovasc Transl Res. 2011; 4:145-153.
22. Nunes S S, Krishnan L, Gerard C S, et al. Angiogenic Potential of Microvessel Fragments Is Independent of the Tissue of Origin and Can Be Influenced by the Cellular Composition of the Implants. Microcirculation. 2010; 17:557-567.
23. Chang C C, Krishnan L, Nunes S S, et al. Determinants of Microvascular Network Topologies in Implanted Neovasculatures. Arterioscler. Thromb. Vasc. Biol. 2011.

24. Mansbridge J N, Liu K, Pinney R E, et al. Growth Factors Secreted by Fibroblasts: Role in Healing Diabetic Foot Ulcers. Diabetes Obes Metab. 1999; 1:265-279.
25. Sawa M, Kuroyanagi Y. Potential of a Cryopreserved Cultured Dermal Substitute Composed of Hyaluronic Acid and Collagen to Release Angiogenic Cytokine. J. Biomater. Sci. Polym. Ed. 2013; 24:224-238.
26. Rehman J, Traktuev D, Li J, et al. Secretion of Angiogenic and Antiapoptotic Factors by Human Adipose Stromal Cells. Circulation. 2004; 109:1292-1298.
27. Kim W S, Park B S, Sung J H, et al. Wound Healing Effect of Adipose-Derived Stem Cells: A Critical Role of Secretory Factors on Human Dermal Fibroblasts. J. Dermatol. Sci. 2007; 48:15-24.
28. Traktuev D O, Prater D N, Merfeld-Clauss S, et al. Robust Functional Vascular Network Formation in Vivo by Cooperation of Adipose Progenitor and Endothelial Cells. Circ. Res. 2009; 104:1410-1420.
29. Ghosh N, Rimoldi O E, Beanlands R S, et al. Assessment of Myocardial Ischaemia and Viability: Role of Positron Emission Tomography. Eur. Heart J. 2010; 31:2984-2995.
30. Assmus B, Schachinger V, Teupe C, et al. Transplantation of Progenitor Cells and Regeneration Enhancement in Acute Myocardial Infarction (Topcare-Ami). Circulation. 2002; 106:3009-3017.
31. Chen S L, Fang W W, Ye F, et al. Effect on Left Ventricular Function of Intracoronary Transplantation of Autologous Bone Marrow Mesenchymal Stem Cell in Patients with Acute Myocardial Infarction. Am. J. Cardiol. 2004; 94:92-95.
32. Strauer B E, Brehm M, Zeus T, et al. Regeneration of Human Infarcted Heart Muscle by Intracoronary Autologous Bone Marrow Cell Transplantation in Chronic Coronary Artery Disease: The Iact Study. J. Am. Coll. Cardiol. 2005; 46:1651-1658.
33. Mazo M, Planat-Benard V, Abizanda G, et al. Transplantation of Adipose Derived Stromal Cells Is Associated with Functional Improvement in a Rat Model of Chronic Myocardial Infarction. Eur J Heart Fail. 2008; 10:454-462.
34. Ragosta M, Powers E R, Samady H, et al. Relationship between Extent of Residual Myocardial Viability and Coronary Flow Reserve in Patients with Recent Myocardial Infarction. Am. Heart J. 2001; 141:456-462.
35. Mazur W, Bitar J N, Lechin M, et al. Coronary Flow Reserve May Predict Myocardial Recovery after Myocardial Infarction in Patients with Timi Grade 3 Flow. Am. Heart J. 1998; 136:335-344.
36. Tang Y L, Zhao Q, Qin X, et al. Paracrine Action Enhances the Effects of Autologous Mesenchymal Stem Cell Transplantation on Vascular Regeneration in Rat Model of Myocardial Infarction. Ann. Thorac. Surg. 2005; 80:229-236; discussion 236-227.
37. Danoviz M E, Nakamuta J S, Marques F L, et al. Rat Adipose Tissue-Derived Stem Cells Transplantation Attenuates Cardiac Dysfunction Post Infarction and Biopolymers Enhance Cell Retention. PLoS One. 2010; 5:e12077.
38. Zhang X, Wang H, Ma X, et al. Preservation of the Cardiac Function in Infarcted Rat Hearts by the Transplantation of Adipose-Derived Stem Cells with Injectable Fibrin Scaffolds. Exp Biol Med (Maywood). 2010; 235:1505-1515.
39. Valina C, Pinkernell K, Song Y H, et al. Intracoronary Administration of Autologous Adipose Tissue-Derived Stem Cells Improves Left Ventricular Function, Perfusion, and Remodelling after Acute Myocardial Infarction. Eur. Heart J. 2007; 28:2667-2677.
40. McCoy L, Tsunoda I, Fujinami R S. Multiple Sclerosis and Virus Induced Immune Responses: Autoimmunity Can Be Primed by Molecular Mimicry and Augmented by Bystander Activation. Autoimmunity. 2006; 39:9-19.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of treating an established myocardial infarction, comprising: providing a stromal vascular fraction construct, the stromal vascular fraction construct consisting of an amount of stromal vascular fraction cells seeded onto a biocompatible substrate; and applying the stromal vascular fraction construct to the site of the established myocardial infarction at a time period of about 2 weeks following a myocardial infarction in a subject.

2. The method of claim 1, wherein applying the stromal vascular fraction construct decreases an amount of fibrosis at the site of the established myocardial infarction.

3. The method of claim 1, wherein applying the stromal vascular fraction construct increases an amount of perfused vessels at the site of the established myocardial infarction.

4. The method of claim 1, wherein applying the stromal vascular fraction construct reduces an amount of myocardial cell death at the site of the established myocardial infarction.

5. The method of claim 1, wherein applying the stromal vascular fraction construct increases an amount of growth factors at the site of the established myocardial infarction.

6. The method of claim 5, wherein the growth factors are selected from the group consisting of vascular endothelial growth factor, transforming growth factor-beta 1, placental growth factor, and basic fibroblast growth factor.

7. The method of claim 6, wherein the growth factor is vascular endothelial growth factor.

8. The method of claim 1, wherein applying the stromal vascular fraction construct to the site of the established myocardial infarction comprises suturing the stromal vascular fraction construct to an epicardial surface of the heart of the subject.

9. The method of claim 1, wherein the biocompatible substrate comprises a polyglactin 910 mesh.

* * * * *